(12) United States Patent
Averback et al.

(10) Patent No.: US 7,544,771 B2
(45) Date of Patent: Jun. 9, 2009

(54) PROTEIN AND ITS USE IN DIAGNOSING ALZHEIMER'S DISEASE

(75) Inventors: Paul Averback, Beaconsfield (CA); Jack Gemmell, Mississauga (CA)

(73) Assignee: Nymox Corporation, St. Laurent, Quebec (CA)

( * ) Notice: Subject to any disclaimer, the term of this patent is extended or adjusted under 35 U.S.C. 154(b) by 0 days.

(21) Appl. No.: 11/064,109

(22) Filed: Feb. 23, 2005

(65) Prior Publication Data
US 2006/0188935 A1     Aug. 24, 2006

(51) Int. Cl.
A61K 38/00    (2006.01)
A61K 39/00    (2006.01)
A61K 39/385   (2006.01)
C07K 16/00    (2006.01)
C12P 21/06    (2006.01)

(52) U.S. Cl. .................. 530/324; 530/300; 424/185.1; 424/193.1; 435/69.1

(58) Field of Classification Search .............. None
See application file for complete search history.

(56) References Cited

U.S. PATENT DOCUMENTS

| 5,830,670 | A  | 11/1998 | de la Monte et al. |
| 5,948,634 | A  | 9/1999  | de la Monte et al. |
| 5,948,888 | A  | 9/1999  | de la Monte et al. |
| 6,770,797 | B2 | 8/2004  | Wands et al.       |
| 2002/0104108 | A1 | 8/2002 | De La Monte et al. |
| 2002/0129391 | A1 | 9/2002 | De La Monte et al. |
| 2003/0033621 | A1 | 2/2003 | De La Monte et al. |
| 2003/0054990 | A1 | 3/2003 | Averback           |
| 2003/0066097 | A1 | 4/2003 | Monte et al.       |

FOREIGN PATENT DOCUMENTS

WO    WO 98/38204    9/1998

*Primary Examiner*—Olga N Chemyshev
(74) *Attorney, Agent, or Firm*—Goodwin Procter LLP

(57) ABSTRACT

Embodiments are directed to a peptide and protein containing that peptide, nucleic acids, antibodies, as well assays detecting the peptide or protein, and methods of identifying patients with or at risk of developing Alzheimer's Disease and other neurodegenerative diseases.

7 Claims, No Drawings

PROTEIN AND ITS USE IN DIAGNOSING ALZHEIMER'S DISEASE

FIELD OF THE INVENTION

Embodiments of the invention are directed to a peptide useful in, for example, binding assays, protein and antibody purification, therapeutics, and diagnostics.

DESCRIPTION OF RELATED ART

Alzheimer's disease (AD) is a presently incurable neurodegenerative disease affecting at least 15 million people worldwide. AD is predominantly a disease of the elderly, with a rate of incidence of about 1% of those aged 65 and rising to an estimated 40% by age 85. As the population as a whole grows older, because of medical advances, increasing life expectancies, and aging of the baby boomer generation, the overall incidence of AD is expected to rise and present even more of a burden to heath care systems and to patients and their caregivers and family.

No effective treatment of AD exists today. Currently available treatments such as Aricept® (donepezil HCl; Pfizer Corp.), Exelon® (rivastigmine tartrate; Novartis Pharmaceuticals Corp.) and Namenda™ and Axura® (memantine; Merz Pharma KgaA and Forest Laboratories, Inc.) are intended to provide a measure of symptomatic relief for patients with mild to moderate AD and do not address the causes of the disease.

Clinical diagnosis of AD is also imperfect; accuracy varies from roughly 50-60% for general practitioners to 80-90% for Alzheimer's disease specialists at referral centers (Molsa et al., *J. Neurol. Neurosurg. Psychiatry*, 48 (11): 1085-90 (1985); Rocca et al., *Ann. Neurol.*, 19:415-424 (1986); Burns et al., *BMJ*, 301(6759):1026 (1990); Risse et al., *Am. J. Psychiatry*, 147(2):168-72 (1990); Gilleard et al., *Acta Psychiatr. Scand.*, 85(4):264-9 (1992); Mendez et al., *Alzheimer Dis. Assoc. Disord.*, 6:35-43 (1992); Fleming et al., *Mayo Clin. Proc.*, 7:1093-1107 (1995); Corey-Bloom et al., *Neurology*, 45:211-218 (1995); and Bowler et al., *J. Neurol. Neurosurg. Psychiatry*, 64(1): 18-24 (1998). There is an average delay of nearly three years from initial symptoms to when the diagnosis of AD is made (Jost et al., *J. Am. Geriatr. Soc.*, 43(11): 1248-55 (1995)).

It has been recognized that a reliable biomarker would be of significant assistance in the accurate and early diagnosis of AD (Growdon et al., *Neurobiol. Aging*, 19:109-116 (1998)). Although several biochemical and genetic markers are currently available, their clinico-pathologic correlations are generally considered too low for routine clinical use. For example, apolipoprotein E ε4 allele is a genetic risk factor which is found only in 50% of AD cases (Myers et al., *Neurology*, 46(3):673-7 (1996)), and tau and β-amyloid protein measurements in cerebrospinal fluid (CSF) and serum Aβ are believed to have significant overlap between AD and non-AD levels, limiting their usefulness (Pirttila et al., *J. Neurol. Sci.*, 127(1):90-5 (1994); Arai et al., *Ann. Neurol.*, 38:649-652 (1995); Jensen et al., *Neurosci. Lett.*, 186(2-3): 189-91 (1995); Motter et al., *Ann. Neurol.*, 38(4):643-8 (1995); Munroe et al., *Ann. Clin. Lab. Sci.*, 25(3):207-17 (1995); Tata et al., *J. Neurol. Neurosurg. Psychiatr.*, 59:280-283 (1995); Vigo-Pelfrey et al., *Neurology*, 45(4):788-93 (1995); Iwatsubo T., *Neurobiol. Aging*, 19:161-163 (1998); Nitsch et al., *Ann. Neurol.*, 37(4):512-8 (1995); van Gool et al., *Ann. Neurol.*, 37(2):277-9 (1995); Tamaoka et al., *J. Neurol. Sci.*, 151 (1-2):65-8 (1996); and Pirtilla et al., *Arch. Neurol.*, 53(2): 189-93 (1996)). Other proposed markers, such as pupillary response to tropicamide (Scinto et al., *Science*, 266:1051-1054 (1994); and Growdon et al., *Arch. Neurol.*, 54(7):841-4 (1997)) and serum factors such as p-97 (Kennard et al., *Nat. Med.*, 2(11): 1230-5 (1996)), have not yet been validated in repeated controlled clinical studies. The major drawbacks of most proposed AD markers are that they are usually not brain-specific molecules associated with AD pathology and that they are not reliably measurable in peripheral fluids.

Neural thread proteins (NTP) are a family of relatively recently characterized brain proteins. NTP is a ~41 kD membrane associated phosphoprotein with functions related to neuritic sprouting and cell death (de la Monte et al., *J. Clin. Invest.*, 100:3093-3104 (1997); and de la Monte et al., *Alz. Rep.*, 2:327-332 (1999)). There is compelling evidence linking NTP with AD. NTP mRNA is upregulated in AD brain compared to controls; NTP protein levels in brain and in CSF are higher in AD than controls; and NTP immunoreactivity is clearly found in senile plaques, in neurofibrillary tangles (NFT), in degenerating neurons, neuropil threads, and dystrophic neuritic sprouts in AD and Down syndrome brains (Ozturk et al., *Proc. Natl. Acad. Sci. USA*, 86:419-423 (1989); de la Monte et al., *J. Clin. Invest.*, 86:1004-13 (1990); de la Monte et al., *J. Neurol. Sci.*, 113:152-64 (1992); de la Monte et al., *Ann. Neurol.*, 32:733-42 (1992); de la Monte et al., *J. Neuropathol. Exp. Neurol.*, 55:1038-50 (1996), de la Monte et al., *J. Neurol. Sci.*, 138:26-35 (1996); de la Monte et al., *J. Neurol. Sci.*, 135:118-25 (1996); de la Monte et al., *J. Clin. Invest.*, 100:3093-3104 (1997); and de la Monte et al., *Alz. Rep.*, 2:327-332 (1999)). NTP accumulation in neurons occurs early in AD neurodegeneration (before NFT formation). NTP has also been identified Down's Syndrome brain tissue (Wands et al., International Patent Publication No. WO 90/06993; de la Monte et al., *Alz. Rep.*, 2:327-332 (1999)). Most patients with Down's Syndrome exhibit neuropathology similar to that of AD after middle age and develop many cognitive defects similar to those of AD later in life. Overexpression of NTP causes neuronal cell death mediated by apoptosis and impaired mitochrondrial function, with activation of the pro-apoptosis pathways observed in brains with AD (de la Monte et al. *J Neuropath Exp Neurol* 60: 195-207 (2001); de la Monte et al. *Cell. Mol. Life Sci.* 58: 844-9 (2001); de la Monte et al. *J Alzheimers Dis.* 6:231-42 (2004)).

NTP levels in the cerebrospinal fluid (CSF) of AD patients and controls were shown to be consistently elevated in AD (Chong et al., *J. Clin. Lab Anal.*, 6(6):379-83 (1992); de la Monte et al., *Ann. Neurol.*, 32:733-742 (1992); de la Monte et al., *J. Clin. Invest.*, 100:3093-3104 (1997); Ghanbari et al., *J. Clin. Lab. Anal.*, 12(4):223-6 (1998); Ghanbari et al., *J. Contemp. Neurol.*, 1998:2-8 (1998); Kahle et al., *Neurology*, 54(7): 1498-504 (2000)). Specificity of NTP elevation in AD was shown in comparison to non-AD neurological disease controls, and NTP elevation was positively correlated with degree of dementia (de la Monte et al., *J. Clin. Invest.*, 100: 3093-3104 (1997); and de la Monte et al., *Alz. Rep.*, 2:327-332 (1999); and Kahle et al., *Neurology*, 54:1498-504 (2000)). In one major study, 89% of patients with early AD had NTP levels of above 2 ng/mL of CSF and 89% of non-AD controls below 2 ng/mL of CSF (de la Monte et al., *J. Clin. Invest.*, 100:3093-3104 (1997)).

Subsequently, the NTP protein was identified in urine by high performance liquid chromatography, capillary electrophoresis, and ELISA (Ghanbari et al., *J. Clin. Lab. Anal.*, 12(4):285-288 (1998); and de la Monte et al., *Alz. Rep.*, 2:327-332 (1999)). Urinary NTP levels were found to correlate with CSF levels in AD patients and controls and to be significantly elevated in AD patients as compared to non-AD patients (Ghanbari et al., *J. Clin. Lab. Anal.*, 12:285-288

(1998) de la Monte et al. *Journal of Alzheimer's Disease* 3: 345-353 (2001)). An assay using gold particles with bound monoclonal anti-NTP in the liquid phase was developed for urine samples and demonstrated to be sensitive and specific for AD (Fitzpatrick et al., *Alzheimer's Reports*, 3:155-159 (2000)). An ELISA-format assay was also developed for urine samples and found to be both highly sensitive and specific for AD (de la Monte et al. *Front Biosci* 7: d989-96 (2002); Munzar et al. *Alzheimer's Reports* 5: 1-6 (2002); Munzar et al. *Neurol Clin Neurophysiol* 2002(1): 2-7 (2002); Munzar et al. *Alzheimer's Reports* 4: 61-65 (2001)).

The cDNA and predicted protein sequence for NTP (AD7c-NTP) has been identified and described (de la Monte et al., *J. Clin. Invest.*, 100:3093-3104 (1997)). Neural thread protein also is described and claimed in U.S. Pat. Nos. 5,948, 634; 5,948,888; and 5,830,670, all for "Neural Thread Protein Gene Expression and Detection of Alzheimer's Disease."

Other species of neural thread protein (~26 kD, ~21 kD, ~17 kD and ~15 kD) have been identified and associated with neuroectodermal tumors, astrocytomas, and glioblastomas and with injury due to hypoxia, ischemia, or cerebral infarction (de la Monte et al., *J. Neuropathol. Exp. Neurol.*, 55:1038-50 (1996), de la Monte et al., *J. Neurol. Sci.*, 138: 26-35 (1996); de la Monte et al., J. Neurol. Sci., 135:118-25 (1996); de la Monte et al., *J. Clin. Invest.*, 100:3093-3104 (1997); and de la Monte et al., *Alz. Rep.*, 2:327-332 (1999)).

SUMMARY

Despite these advancements, there is a need to develop improved assays and protein or peptide components useful in the assays. There also is a need to improve upon the existing assays and biomarkers for AD and other neurodegenerative diseases. Technical advances such as methods to routinely purify native peptide markers from urine in a cost-effective manner would also improve any such assays.

There also is a need in the art for improved compositions useful in therapeutics and diagnostics related to AD and Down's Syndrome, and for compositions useful in therapeutics and diagnostics for neuroectodermal tumors, astrocytomas, glioblastomas, and other neurodegenerative disorders and for injury due to hypoxia, ischemia and cerebral infarction.

An embodiment of the present invention provides a peptide having the amino acid sequence of SEQ ID NO:14.

A further embodiment of the present invention provides a peptide encoded by the nucleic acid sequence of SEQ ID NO:15 or by a sequence that hybridizes to the nucleic acid sequence of SEQ ID NO:15 under stringent conditions.

An even further embodiment of the present invention provides a composition comprising a peptide having the amino acid sequence of SEQ ID NO:14. A still further embodiment of the present invention provides a polynucleotide having the nucleic acid sequence of SEQ ID NO:15. Another embodiment of the present invention provides a polynucleotide that encodes an amino acid sequence of SEQ ID NO:14.

Another embodiment of the invention provides a protein other than AD7c-NTP that contains the amino acid sequence of SEQ ID NO:14. Further embodiments include proteins encoded by a DNA comprising at least a nucleic acid sequence of SEQ ID NO: 15, or by a sequence that hybridizes to a DNA comprising at least a nucleic acid sequence of SEQ ID NO:15.

Yet another embodiment of the present invention provides a method for detecting the peptide having the amino acid sequence of SEQ ID NO:14 from a biological sample, as well as a method of identifying a protein other than AD7c-NTP that contains the amino acid sequence of SEQ ID NO:14, the method comprising:

(1) contacting a biological sample with one or more peptides or antibodies that bind to the peptide having the amino acid sequence of SEQ ID NO:14 and/or a protein other than AD7c-NTP that contains the amino acid sequence of SEQ ID NO:14, thereby forming peptide or antibody conjugates containing the respective bound entities;

(2) isolating the resulting peptide or antibody; and (3) separating the peptide having the amino acid sequence of SEQ ID NO:14 and/or a protein other than AD7c-NTP that contains the amino acid sequence of SEQ ID NO:14 from the peptide and/or antibody conjugates to obtain a purified peptide having the amino acid sequence of SEQ ID NO:14, or a purified protein other than AD7c-NTP containing the amino acid sequence of SEQ ID NO:14.

A further embodiment of the present invention provides an antibody that specifically recognizes (a) a peptide having the amino acid sequence of SEQ ID NO:14; (b) a peptide encoded by the nucleic acid sequence of SEQ ID NO:15; or (c) a peptide encoded by a nucleic acid sequence that hybridizes under stringent conditions to the nucleic acid sequence of SEQ ID NO:15.

An additional embodiment provides an antibody that specifically recognizes (a) a protein other than AD7c-NTP that includes an amino acid sequence of SEQ ID NO:14; (b) a protein other than AD7c-NTP encoded by a DNA containing the nucleic acid sequence of SEQ ID NO:15; or (c) a protein other than AD7c-NTP encoded by a DNA containing a nucleic acid sequence that hybridizes under stringent conditions to the nucleic acid sequence of SEQ ID NO:15.

An even further embodiment provides a method for detecting or purifying from a biological sample a peptide having the amino acid sequence of SEQ ID NO:14 and/or a protein other than AD7c-NTP that contains the amino acid sequence of SEQ ID NO:14 comprising:

(1) contacting a biological sample with one or more conjugating peptides having an amino acid sequence selected from the group consisting of:
  (a) H H A R L; (SEQ ID NO: 1);
  (b) H A R L; (SEQ ID NO: 2);
  (c) H A R L I; (SEQ ID NO: 3);
  (d) H A R L I L; (SEQ ID NO: 12);
  (e) H H A R L C L; (SEQ ID NO: 13);
  (f) A R L I L; (SEQ ID NO: 16);
  (g) H H A R L I F; (SEQ ID NO: 17);
  (h) T H A R L I L; (SEQ ID NO: 18);
  (i) A R L I; (SEQ ID NO: 19);
  (j) A R L; (SEQ ID NO: 20);
  (k) H A R L C L; (SEQ ID NO: 21);
  (l) A R L C L; (SEQ ID NO: 22);
  (m) A R C L; (SEQ ID NO: 23);
  (n) M F A R L I L; (SEQ ID NO: 24);
  (o) F A R L I L; (SEQ ID NO: 25);
  (p) F A R L I; (SEQ ID NO: 26);
  (q) F A R L; (SEQ ID NO: 27);
  (r) H A R L I F; (SEQ ID NO: 28);
  (s) A R L I F; (SEQ ID NO: 29); and homologs of such amino acid sequences to form conjugates of at least (A) the one or more conjugating peptides and (B) a peptide having the amino acid sequence of SEQ ID NO:14 and/or a protein other than AD7c-NTP that contains the amino acid sequence of SEQ ID NO:14;

(2) isolating the resulting conjugates; and (3) separating the peptide having the amino acid sequence of SEQ ID NO:14 and/or a protein other than AD7c-

NTP that contains the amino acid sequence of SEQ ID NO:14 from the conjugate to obtain a purified peptide having the amino acid sequence of SEQ ID NO:14 and/or a protein other than AD7c-NTP that contains the amino acid sequence of SEQ ID NO:14.

A still further embodiment of the present invention provides a method for detecting or purifying from a biological sample a peptide having the amino acid sequence of SEQ ID NO:14 and/or a protein other than AD7c-NTP that contains the amino acid sequence of SEQ ID NO:14 comprising:

(1) contacting a biological sample with one or more conjugating peptides having an amino acid sequence selected from the group consisting of:
  (a) L H A R L C L A N F C G R N R V (SEQ ID NO: 4);
  (b) L A R L C L A N F C G N N N V (SEQ ID NO: 5);
  (c) C A R Y R T G H H A R L M (SEQ ID NO: 6);
  (d) H H A R L P L A N F C G (SEQ ID NO: 7);
  (e) R T G H H A R L C*L A N F C (SEQ ID NO: 8);
  (f) C E S A R Y R T G H H A R L C* (SEQ ID NO: 9);
  (g) D N T H H A R L I L (SEQ ID NO: 10);
  (h) S H H A R L I L (SEQ ID NO: 11); and homologs thereof, thereby forming conjugates comprising at least (A) the one or more conjugating peptides, and (B) a peptide having the amino acid sequence of SEQ ID NO:14 and/or a protein other than AD7c-NTP that contains the amino acid sequence of SEQ ID NO:14;

(2) isolating the resulting conjugates; and
(3) separating the peptide having the amino acid sequence of SEQ ID NO:14 and/or the protein other than AD7c-NTP that contains the amino acid sequence of SEQ ID NO:14 from the conjugates to obtain a purified peptide having the amino acid sequence of SEQ ID NO:14 and/or a protein other than AD7c-NTP that contains the amino acid sequence of SEQ ID NO:14.

Another embodiment provides a method for detecting or purifying from a biological sample a peptide having the amino acid sequence of SEQ ID NO:14 and/or a protein other than AD7c-NTP that contains the amino acid sequence of SEQ ID NO:14 comprising:

(a) contacting a biological sample with one or more conjugating peptides having an amino acid sequence selected from the group consisting of:
  (i) A R L I (SEQ ID NO: 19);
  (ii) H A R L (SEQ ID NO: 2);
  (iii) F A R L (SEQ ID NO: 27);
  (iv) A R L (SEQ ID NO: 20); and
  (v) A R L C (SEQ ID NO: 30);
    wherein the peptide comprises at least one and up to 25 additional amino acids flanking either the 3' or 5' end of the peptide, thereby forming conjugates comprising at least (A) one or more conjugating peptides, and (B) a peptide having the amino acid sequence of SEQ ID NO:14 and/or a protein other than AD7c-NTP that contains the amino acid sequence of SEQ ID NO:14;

(b) isolating the resulting conjugates; and
(c) separating the peptide having the amino acid sequence of SEQ ID NO:14 and/or the protein other than AD7c-NTP that contains the amino acid sequence of SEQ ID NO:14 from the conjugates to obtain a purified peptide having the amino acid sequence of SEQ ID NO:14 and/or a protein other than AD7c-NTP that contains the amino acid sequence of SEQ ID NO:14.

Other embodiments provide a diagnostic test for determining the presence of Alzheimer's Disease or other neurodegenerative disorder comprising determining the amount of peptide having the amino acid sequence of SEQ ID NO:14 and/or the protein other than AD7c-NTP that contains the amino acid sequence of SEQ ID NO:14 present in a biological sample, and then determining whether the amount of peptide and/or protein present in the sample is above a threshold amount indicative of the presence of Alzheimer's Disease or other neurodegenerative disorder.

Another embodiment provides a diagnostic test for determining the presence of Alzheimer's Disease or other neurodegenerative disorder comprising any of the aforementioned methods of detecting or purifying from a biological sample the peptide having the amino acid sequence of SEQ ID NO:14 and/or the protein other than AD7c-NTP that contains the amino acid sequence of SEQ ID NO:14. The method further includes determining the amount of peptide having the amino acid sequence of SEQ ID NO:14 and/or the protein other than AD7c-NTP that contains the amino acid sequence of SEQ ID NO:14 present in the sample, and then determining whether the amount of peptide and/or protein present in the sample is above a threshold amount indicative of the presence of Alzheimer's Disease or other neurodegenerative disorder.

Both the foregoing general description and the following detailed description are exemplary and explanatory and are intended to provide further explanation of the invention as claimed. Other features and advantages will be readily apparent to those skilled in the art from the following detailed description of the preferred embodiments. Moreover, the description herein of any disadvantages or deleterious properties associated with know systems, compositions, and methods is in no way intended to limit the scope of the embodiments described herein to their exclusion. Indeed, various embodiments of the invention may include one or more known systems, composition, or methods, without suffering from the disadvantages or deleterious properties.

DETAILED DESCRIPTION OF THE PREFERRED EMBODIMENTS

Embodiments of the invention are directed to a novel peptide associated with Alzheimer's Disease (AD) and related neurodegenerative diseases. The peptide was unexpectedly found to act as a reliable biomarker for the accurate and early diagnosis of AD. The novel peptide is useful in assays and diagnostic tests for AD, as well as in therapeutics for treating AD and other conditions.

According to an implementation of an embodiment, the peptide is represented by the following amino acid sequence (SEQ ID NO:14) and is encoded by the indicated nucleic acid sequence (SEQ ID NO:15).

| Nucleic Acid Sequence (SEQ ID NO:15) and Amino Acid Sequence (SEQ ID NO:14) |
|---|
| ATC TCT GGA CCT TGT GAT CTG CCT GCC TCG GCC TCC CAA AGT GCT |
| I    S    G    P    C    D    L    P    A    S    A    S    Q    S    A |
| GGG ATT ACA GGC GTG AGC CAC CAC GCC CGG CTT ATT TTT AAT TTT |
| G    I    T    G    V    S    H    H    A    R    L    I    F    N    F |
| TGT TTG TTT GAA ATG GAA TCT CAC |
| C    L    F    E    M    E    S    H |

While not intending to be bound by any theory of operation, the inventors believe that the peptide represented by the amino acid sequence of SEQ ID NO: 14 provides an unexpectedly improved binding affinity for the conjugating peptides described in this disclosure. Consequently, this peptide can be used to characterize urine samples and differentiate individuals with Alzheimer's Disease from control subjects, when used in an assay with a standard curve derived from the same or similar peptides or polypeptides having the amino acid sequence of SEQ ID NO: 14.

Embodiments also contemplate peptides encoded by a nucleic acid sequence that hybridizes to the nucleic acid sequence of SEQ ID NO:15 under stringent conditions. In accordance with an implementation of the present invention, the stringent conditions are high stringency southern hybridization conditions.

In addition to the peptides and polynucleotides of the embodiments, the embodiments further contemplate antibodies to the peptides and proteins, inhibitors of the peptides and/or polynucleotides and/or proteins other than AD7c-NTP that include the peptides, compositions that comprise the peptides, polynucleotides, antibodies and inhibitors, and methods of using any of the foregoing for diagnosing and/or treating a condition in a patient, such as diagnosing AD.

The expression "AD7c-NTP" refers to the ~41 kD protein and the cDNA and the nucleic acid sequences coding for it described in de la Monte et al., *J. Clin. Invest.*, 100:3093-104 (1997), in Sequences 120 and 121 of U.S. Pat. Nos. 5,948,634, 5,948,888, and 5,830,670 and in GenBank #AF010144. Accordingly, the expression "protein other than AD7c-NTP" refers to a protein that does not have the identical amino acid sequence reported in the above-mentioned publications.

The expression "peptide" as it is used herein includes the specific peptide amino acid sequence, as well as homologs, derivatives, variants, fragments, fusion proteins, and peptide mimetics of these specifically listed peptides and their corresponding nucleic acid sequences.

The term "fragment" refers to a protein or polypeptide that consists of a continuous subsequence of the amino acid sequence of protein or peptide and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same protein or peptide, with a contiguous amino acid sequence in common or not, joined together, either directly or through a linker.

The term "variant" refers to a protein or polypeptide in which one or more amino acid substitutions, deletions, and/or insertions are present as compared to the amino acid sequence of the proteins or peptides described herein and includes naturally occurring allelic variants or alternative splice variants of the so-described protein or peptide. The term "variant" includes the replacement of one or more amino acids in a peptide sequence with a similar or homologous amino acid(s) or a dissimilar amino acid(s). There are many scales on which amino acids can be ranked as similar or homologous. (Gunnar von Heijne, *Sequence Analysis in Molecular Biology*, p. 123-39 (Academic Press, New York, N.Y. 1987.) Preferred variants include alanine substitutions at one or more of amino acid positions. Other preferred substitutions include conservative substitutions that have little or no effect on the overall net charge, polarity, or hydrophobicity of the protein. Conservative substitutions are set forth in Table 2 below.

TABLE 2

Conservative Amino Acid Substitutions

| | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | proline |
| | methionine |
| | leucine |
| | isoleucine |

Table 3 sets out another scheme of amino acid substitution:

TABLE 3

| Original Residue | Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include proteins and peptides with additional amino acid residues before or after the protein or peptide amino acid sequence on linker peptides. For example, a cysteine residue may be added at both the amino and carboxy terminals of a in order to allow the cyclisation of the by the formation of a di-sulphide bond. The term "variant" also encompasses polypeptides that have the amino acid sequence of a peptide with at least one and up to 25 or more additional amino acids flanking either the 3' or 5' end of the peptide.

The term "derivative" refers to a chemically modified protein or polypeptide that has been chemically modified either by natural processes, such as processing and other post-translational modifications, but also by chemical modification techniques, such as, for example, by addition of one or more polyethylene glycol molecules, sugars, phosphates, and/or other such molecules, where the molecule or molecules are not naturally attached to wild-type protein or peptide. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *Proteins—Structure And Molecular Properties*, 2nd Ed., T. E. Creighton, W. H. Freeman and Company, New York (1993) and Wold, F., "Posttranslational Protein Modifications: Perspectives and Prospects," pgs. 1-12 in *Posttranslational Covalent Modification Of Proteins*, B. C. Johnson, Ed., Academic Press, New York (1983); Seifter et al., *Meth. Enzymol.* 182: 626-646 (1990) and Rattan et al., "Protein Synthesis: Post-translational Modifications and Aging," Ann. N.Y. Acad. Sci. 663: 48-62 (1992). The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "homolog" refers to a protein that is at least 60 percent identical in its amino acid sequence of a protein or peptide described herein, as the case may be, as determined by standard methods that are commonly used to compare the similarity in position of the amino acids of two polypeptides. The degree of similarity or identity between two proteins can be readily calculated by known methods, including but not limited to those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; *Sequence Analysis Primer*, Gribskov, M. and Devereux, J., eds., M Stockton Press, New York, 1991; and Carillo H. and Lipman, D., SIAM, *J. Applied Math.*, 48: 1073 (1988). Preferred methods to determine identity are designed to give the largest match between the sequences tested. Methods to determine identity and similarity are codified in publicly available computer programs.

Preferred computer program methods useful in determining the identity and similarity between two sequences include, but are not limited to, the GCG program package (Devereux, J., et al., *Nucleic Acids Research*, 12(1): 387 (1984)), BLASTP, BLASTN, and FASTA, Atschul, S. F. et al., *J. Molec. Biol.*, 215: 403-410 (1990). The BLAST X program is publicly available from NCBI and other sources (BLAST Manual, Altschul, S., et al., NCBI NLM NIH Bethesda, Md. 20894; Altschul, S., et al., *J. Mol. Biol.*, 215: 403-410 (1990). By way of example, using a computer algorithm such as GAP (Genetic Computer Group, University of Wisconsin, Madison, Wis.), the two proteins or polypeptides for which the percent sequence identity is to be determined are aligned for optimal matching of their respective amino acids (the "matched span", as determined by the algorithm).

A gap opening penalty (which is calculated as 3×(times) the average diagonal; the "average diagonal" is the average of the diagonal of the comparison matrix being used; the "diagonal" is the score or number assigned to each perfect amino acid by the particular comparison matrix) and a gap extension penalty (which is usually $1/10$ times the gap opening penalty), as well as a comparison matrix such as PAM 250 or BLOSUM 62 are used in conjunction with the algorithm. A standard comparison matrix (see Dayhoff et al. in: *Atlas of Protein Sequence and Structure*, vol. 5, supp.3 [1978] for the PAM250 comparison matrix; see Henikoff et al., *Proc. Natl. Acad. Sci USA*, 89:10915-10919 [1992] for the BLOSUM 62 comparison matrix) also may be used by the algorithm. The percent identity then is calculated by the algorithm. Homologs will typically have one or more amino acid substitutions, deletions, and/or insertions as compared with the corresponding protein or peptide, as the case may be.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to this invention provide a spatial arrangement of reactive chemical moieties that closely resemble the three-dimensional arrangement of active groups in the peptide on which the peptide mimetic is based. As a result of this similar active-site geometry, the peptide mimetic has effects on biological systems that are similar to the biological activity of the peptide.

The peptide mimetics of the embodiments preferably are substantially similar in both three-dimensional shape and biological activity to the peptides described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is described in the paper "Tritriated D-ala$^1$-Peptide T Binding", Smith C. S. et al., *Drug Development Res.*, 15, pp. 371-379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is provided in conformationally restricted thymopentin-like compounds, such as those disclosed in U.S. Pat. No. 4,457,489 (1985), Goldstein, G. et al., the disclosure of which is incorporated by reference herein in its entirety. A third method is to substitute peptide bonds in the peptide by pseudopeptide bonds that confer resistance to proteolysis.

A number of pseudopeptide bonds have been described that in general do not affect peptide structure and biological activity. One example of this approach is to substitute retroinverso pseudopeptide bonds ("Biologically active retroinverso analogues of thymopentin", Sisto A. et al in Rivier, J. E. and Marshall, G. R. (eds) "Peptides, Chemistry, Structure and Biology", *Escom, Leiden* (1990), pp. 722-773) and Dalpozzo, et al. (1993), *Int. J. Peptide Protein Res.*, 41:561-566, incorporated herein by reference). According to this modification, the amino acid sequences of the peptides may be identical to the sequences of a peptide described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), *Int. J. Peptide Protein Res.*, 41:181-184, incorporated herein by reference in its entirety).

Thus, the amino acid sequences of these peptides may be identical to the sequences of a peptide, except that one or more of the peptide bonds are replaced by an isostere pseudopeptide bond. The expression "amino acid sequence(s)" preferably is used herein to denote a sequence of at least two amino acids, preferably at least four, and more preferably at least five. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of the peptides described herein represent another class of peptide mimetics that retain the important structural determinants for biological activity, yet eliminate the peptide bonds, thereby conferring resistance to proteolysis (Simon, et al., 1992, *Proc. Natl. Acad. Sci. USA*, 89:9367-9371, incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the peptides may be replaced with the N-substituted glycine corresponding to the replaced amino acid.

The expression "peptide mimetic" or "mimetic" also includes reverse-D peptides and enantiomers as defined below. The phrase "reverse-D peptide" refers to a biologically active protein or peptide consisting of D-amino acids arranged in a reverse order as compared to the L-amino acid sequence of an NTP peptide. Thus, the carboxy terminal residue of an L-amino acid NTP peptide becomes the amino terminal for the D-amino acid peptide and so forth. For example, the NTP peptide, SSWDY (SEQ ID NO: 31), becomes $Y_d D_d W_d S_d S_d$, where $D_d$, $S_d$, $W_d$, and $Y_d$ are the D-amino acids corresponding to the L-amino acids, D, S, W, and Y respectively.

One embodiment provides a peptide is represented by the following amino acid sequence (SEQ ID NO:14), that is encoded by the indicated nucleic acid sequence (SEQ ID NO:15).

Nucleic Acid Sequence (SEQ ID NO:15) and Amino Acid Sequence (SEQ ID NO:14)

| ATC | TCT | GGA | CCT | TGT | GAT | CTG | CCT | GCC | TCG | GCC | TCC | CAA | AGT | GCT |
|---|---|---|---|---|---|---|---|---|---|---|---|---|---|---|
| I | S | G | P | C | D | L | P | A | S | A | S | Q | S | A |
| GGG | ATT | ACA | GGC | GTG | AGC | CAC | CAC | GCC | CGG | CTT | ATT | TTT | AAT | TTT |
| G | I | T | G | V | S | H | H | A | R | L | I | F | N | F |
| TGT | TTG | TTT | GAA | ATG | GAA | TCT | CAC | | | | | | | |
| C | L | F | E | M | E | S | H | | | | | | | |

In addition to the peptides and polynucleotides of the embodiments, the embodiments further contemplate antibodies to the peptides and proteins, inhibitors of the peptides and/or polynucleotides and/or proteins other than AD7c-NTP that include the peptides, compositions that comprise the peptides, polynucleotides, antibodies and inhibitors, and methods of using any of the foregoing for diagnosing and/or treating a condition in a patient, such as diagnosing AD.

Embodiments contemplate recombinant peptides and proteins (and the nucleic acid sequences encoding the peptides and proteins), peptides and proteins that are isolated from their natural source, as well as synthetically manufactured peptides and proteins. Methods of preparing recombinant peptides and proteins are well known in the art. The recombinant peptides and proteins may be prepared in any suitable manner as would be known to a person skilled in the art.

The peptides are contemplated to be of varying purity ranging from impure to pure. Preferably, the peptides are substantially pure. Methods for purifying peptides are well known in the art. The peptides may be purified by any suitable manner as would be known by a person skilled in the art.

Also contemplated are peptides that are isolated from other amino acids and compounds, as well as peptides that are flanked on one or both sides by additional amino acids and/or conjugated to other compounds, including additional peptides. Another embodiment provides a protein other than AD7c-NTP that contains the amino acid sequence of SEQ ID NO:14. Further embodiments include proteins encoded by a DNA comprising at least a nucleic acid sequence of SEQ ID NO:15, or by a sequence that hybridizes to a DNA comprising at least a nucleic acid sequence of SEQ ID NO:15.

According to an implementation of the invention, the peptide or protein may conjugated to an additional peptide ("conjugating peptide") selected from the group consisting of:

(a) H H A R L (SEQ ID NO: 1);
(b) H A R L (SEQ ID NO: 2);
(c) H A R L I (SEQ ID NO: 3);
(d) H A R L I L (SEQ ID NO: 12);

(e) H H A R L C L (SEQ ID NO: 13);
(f) A R L I L (SEQ ID NO: 16);
(g) H H A R L I F (SEQ ID NO: 17);
(h) T H A R L I L (SEQ ID NO: 18);
(i) A R L I (SEQ ID NO: 19);
(j) A R L (SEQ ID NO: 20);
(k) H A R L C L (SEQ ID NO: 21);
(l) A R L C L (SEQ ID NO: 22);
(m) A R C L (SEQ ID NO: 23);
(n) M F A R L I L (SEQ ID NO: 24);
(o) F A R L I L (SEQ ID NO: 25);
(p) F A R L I (SEQ ID NO: 26);
(q) F A R L (SEQ ID NO: 27);
(r) H A R L I F (SEQ ID NO: 28);
(s) A R L I F (SEQ ID NO: 29); and homologs, derivatives and variants thereof.

Certain embodiments contemplate the use of a sequence, referred to as "the Harlil sequence" or a peptide, referred to as "a Harlil peptide," as follows for detecting the presence in a biological sample of the peptide of SEQ ID NO: 14, or protein other than AD7c-NTP containing the peptide of SEQ ID NO: 14:
 (a) T H A R L I L (SEQ ID NO: 18)
 (b) H H A R L C L (SEQ ID NO: 13)
 (c) M F A R L I L (SEQ ID NO: 24)
 (d) H H A R L I F (SEQ ID NO: 17)

Embodiments encompass the use of peptides having the sequence of any of regions (a), (b), (c), (d), or homologs, derivatives or variants of these (including but not limited to "H A R L M L" SEQ ID NO: 32). The Harlil peptides also can have additional amino acid residues before or after the Harlil sequence on linker peptides. Thus, a Harlil peptide for use in embodiments includes the peptide G I T G M C T H A R L I L Y F F L V (SEQ ID NO: 33). The peptides may include flanking sequences. Preferably, the Harlil peptide having additional amino acid residues does not exceed 25 total amino acid residues in length.

Homologs, derivatives and variants of the Harlil peptides are also encompassed for use in embodiments of the invention.

According to another implementation, the peptide is conjugated to an additional peptide ("conjugating peptide") selected from the group consisting of:
 (a) L H A R L C L A N F C G R N R V (SEQ ID NO:4);
 (b) L A R L C L A N F C G N N N V (SEQ ID NO:5);
 (c) C A R Y R T G H H A R L M (SEQ ID NO:6);
 (d) H H A R L P L A N F C G (SEQ ID NO:7);
 (e) R T G H H A R L C*L A N F C (SEQ ID NO:8);
 (f) C E S A R Y R T G H H A R L C * (SEQ ID NO:9);
 (g) D N T H H A R L I L (SEQ ID NO:10);
 (h) S H H A R L I L (SEQ ID NO:11); and homologs, derivatives and variants thereof.

According to another embodiment, the peptide is conjugated to a non-peptide compound. All of these peptides to which the peptide of SEQ ID NO: 14, or protein other than AD7c-NTP containing the peptide of SEQ ID NO: 14 may be conjugated to are referred to herein as "conjugating peptides." Thus, the embodiments described herein include assays using the above-mentioned conjugating peptides that are capable of conjugating to a peptide of SEQ ID NO: 14, to detect the peptide, to detect proteins other than AD7c-NTP that contain the peptide, to detect fragments and variants of the peptide, and to diagnose Alzheimer's Disease. Additional embodiments described herein include assays using antibodies that are capable of conjugating to a peptide of SEQ ID NO: 14 or proteins other than AD7c-NTP that contain a peptide of SEQ ID NO: 14, to detect the peptide, to detect proteins other than AD7c-NTP that contain the peptide, to detect fragments and variants of the peptide, and to diagnose Alzheimer's Disease.

This invention also provides proteins, peptides and other compounds which are homologs, variants and/or derivatives of a conjugating peptide.

Embodiments contemplate compositions comprising the peptide or protein described in the embodiments (collectively, the peptide having the amino acid sequence of SEQ ID NO:14, protein other than AD7c-NTP having a peptide with the amino acid sequence of SEQ ID NO:14, the amino acid sequence encoded by the nucleic acid sequence of SEQ ID NO:15, protein encoded by DNA having at least the nucleic acid sequence of SEQ ID NO:15, the amino acid sequence encoded by a nucleic acid sequence that hybridizes under stringent conditions to the nucleic acid sequence of SEQ ID NO:15, and protein encoded by DNA having at least a nucleic acid sequence that hybridizes under stringent conditions to the nucleic acid sequence of SEQ ID NO:15). Also contemplated are the use of compositions comprising Harlil peptides, peptide mimetics, binding partners, and/or homologs, derivatives or variants as affinity binding partners of the peptide and protein of the present invention for assay or purification of the peptide or protein biomarker, the use of Harlil peptides, peptide mimetics, and homologs, derivatives or variants thereof to block the Harlil peptide sites on the peptide or protein, or the use of substances that interact with the peptide or protein through the Harlil sequences. Also encompassed are antibodies directed to the peptide or protein described in the embodiments, the Harlil peptide sequences, and nucleic acids corresponding to the peptide, the Harlil peptides and homologs, derivatives or variants thereof.

Any suitable carrier, binder, diluent, etc. may be used in the compositions of the present invention as would be known to persons skilled in the art, without limitation.

The Harlil sequence shows binding specificity to the peptide and protein described in the embodiments. When a Harlil peptide or other "conjugating peptide" or a homolog, derivative or variant thereof, is immobilized it can be used to purify the peptide or proteins of the embodiments from solutions. When it is used to capture the peptide or protein of the embodiments as part of an affinity assay, the binding to the peptide is very specific and is unaffected by pH from 3.5 through pH 8. The sensitivity of this affinity assay is at least as high as an immunoassay. For example, a positive urine pool which contains about 0.5 ng/mL of peptide or protein by ELISA can be diluted almost 4 fold and still be differentiated from a negative pool by this affinity assay. Moreover, assay sensitivity can be improved by using a more sensitive detection means, such as by using fluorescent or chemoluminescent substrates or radio-labeled assays.

Because the Harlil peptides (or conjugating peptides) bind specifically to the peptide or protein described herein, they can be used in diagnostic assays for detecting the presence of the peptide or antibodies to the peptide in a biological sample. Above normal levels of the peptide and/or protein described herein in bodily fluids is shown herein by the present inventor to indicate the presence of AD, Down's Syndrome, or other degenerative brain disease. According to an implementation of and embodiment of the present invention, a concentration in urine of the peptide of the invention of at least about 22 µg/ml indicates the presence of AD.

Because of its unique self-binding characteristic, a Harlil peptide can be used as an analog to the peptide described in the embodiments of the invention in an assay. In a sequential or competitive assay, the peptide described herein will bind to the Harlil peptide conjugate solid phase, and remain on during washes where it blocks the binding of immunoglobulin (such as rabbit IgG). The Harlil peptides can also be used as a capture antibody replacement in a sandwich assay.

It is believed that the peptide of the embodiments participates in the neurodegenerative cascade. The ability to interrupt or redirect the cascade by targeting the peptide offers a therapeutic opportunity. For example, it may be possible to intervene therapeutically by using the ability of the Harlil peptides to interact with the peptide, thus blocking the reactive site. Alternatively, the Harlil peptides and mimetics may be useful to target drugs to cells expressing the Harlil sequence.

Antibodies useful in various embodiments described herein include polyclonal antibodies, monoclonal antibodies, chimeric antibodies, and anti-idiotypic antibodies. Polyclonal antibodies are heterogeneous populations of antibody molecules derived from the sera of animals immunized with an antigen. Monoclonal antibodies are a substantially homogeneous population of antibodies to specific antigens. Monoclonal antibodies may be obtained by methods known to those skilled in the art, e.g., Kohler and Milstein, 1975, *Nature* 256:495-497 and U.S. Pat. No. 4,376,110. Such antibodies may be of any immunoglobulin class including IgG, IgM, IgE, IgA, GILD and any subclass thereof.

Chimeric antibodies are molecules, different portions of which are derived from different animal species, such as those having variable region derived from a murine monoclonal antibody and a human immunoglobulin constant region. Chimeric antibodies and methods for their production are known in the art (Cabilly et al., 1984, *Proc. Natl. Acad. Sci. USA* 81:3273-3277; Morrison et al., 1984, *Proc. Natl. Acad. Sci. USA* 81:6851-6855; Boulianne et al., 1984, *Nature* 312:643-646; Cabilly et al., European Patent Application 125023 (published Nov. 14, 1984); Taniguchi et al., European Patent Application 171496 (published Feb. 19, 1985); Morrison et al., European Patent Application 173494 (published Mar. 5, 1986); Neuberger et al., PCT Application WO 86/01533 (published Mar. 13, 1986); Kudo et al., European Patent Application 184187 (published Jun. 11, 1986); Morrison et al., European Patent Application 173494 (published Mar. 5, 1986); Sahagan et al., 1986, *J. Immunol.* 137:1066-1074; Robinson et al., PCT/US86/02269 (published May 7, 1987); Liu et al., 1987, *Proc. Natl. Acad. Sci. USA* 84:3439-3443; Sun et al., 1987, *Proc. Natl. Acad. Sci. USA* 84:214-218; Better et al., 1988, *Science* 240:1041-1043). These references are hereby incorporated by reference in their entirety.

An anti-idiotypic (anti-Id) antibody is an antibody that recognizes unique determinants generally associated with the antigen-binding site of an antibody. An anti-Id antibody is prepared by immunizing an animal of the same species and genetic type (e.g., mouse strain) as the source of the monoclonal antibody with the monoclonal antibody to which an anti-Id is being prepared. The immunized animal will recognize and respond to the idiotypic determinants of the immunizing antibody by producing an antibody to these isotypic determinants (the anti-Id antibody).

Accordingly, monoclonal antibodies generated against the peptides, proteins, or polypeptides of the embodiments may be used to induce anti-Id antibodies in suitable animals. Spleen cells from such immunized mice can be used to produce anti-Id hybridomas secreting anti-Id monoclonal antibodies. Further, the anti-Id antibodies can be coupled to a carrier such as keyhole limpet hemocyanin (KLH) and used to immunize additional BALB/c mice. Sera from these mice will contain anti-anti-Id antibodies that have the binding properties of the final mAb specific for an R-PTPase epitope. The anti-Id antibodies thus have their idiotypic epitopes, or "idiotopes" structurally similar to the epitope being evaluated, such as *Streptococcus pyogenes* polypeptides.

The term "antibody" also is meant to include both intact molecules as well as fragments such as Fab which are capable of binding antigen. Fab fragments lack the Fc fragment of intact antibody, clear more rapidly from the circulation, and may have less non-specific tissue binding than an intact antibody (Wahl et al., 1983, *J. Nucl. Med.* 24:316-325). It will be appreciated that Fab and other fragments of the antibodies useful in the embodiments may be used for the detection and quantitation of *N. meningitidis* polypeptides according to the methods for intact antibody molecules.

The antibodies are used in a variety of ways, e.g., for confirmation that a protein is expressed, or to confirm where a protein is expressed. Labeled antibody (e.g., fluorescent labeling for FACS) can be incubated with intact bacteria and the presence of the label on the bacterial surface confirms the location of the protein, for instance.

Antibodies generated against the peptides or proteins described herein can be obtained by administering the peptides or proteins or epitope-bearing fragments, analogs, or cells to an animal using routine protocols. For preparing monoclonal antibodies, any technique that provides antibodies produced by continuous cell line cultures are used.

Embodiments include polynucleotides that encode the peptides and proteins described in the embodiments. Preferably, the polynucleotide has the nucleic acid sequence of SEQ ID NO:15, or a polynucleotide including the nucleic acid sequence of SEQ ID NO:15. Embodiments of the invention also include polynucleotides capable of hybridizing under reduced stringency conditions, more preferably stringent conditions, and most preferably highly stringent conditions, to the polynucleotides described herein. Examples of stringency conditions are shown in the Stringency Conditions Table below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE I

STRINGENCY CONDITIONS

| Stringency Condition | Polynucleotide Hybrid | Hybrid Length (bp)$^f$ | Hybridization Temperature and Buffer$^H$ | Wash Temperature and Buffer$^H$ |
|---|---|---|---|---|
| A | DNA:DNA | >50 | 65EC; 1 × SSC -or- 42EC; 1 × SSC, 50% formamide | 65EC; 0.3 × SSC |
| B | DNA:DNA | <50 | $T_B$; 1 × SSC | $T_B$; 1 × SSC |
| C | DNA:RNA | >50 | 67EC; 1 × SSC -or- 45EC; 1 × SSC, 50% formamide | 67EC; 0.3 × SSC |
| D | DNA:RNA | <50 | $T_D$; 1 × SSC | $T_D$; 1 × SSC |
| E | RNA:RNA | >50 | 70EC; 1 × SSC -or- 50EC; 1 × SSC, 50% formamide | 70EC; 0.3 × SSC |
| F | RNA:RNA | <50 | $T_F$; 1 × SSC | $T_F$; 1 × SSC |
| G | DNA:DNA | >50 | 65EC; 4 × SSC -or- 42EC; 4 × SSC, 50% formamide | 65EC; 1 × SSC |
| H | DNA:DNA | <50 | $T_H$; 4 × SSC | $T_H$; 4 × SSC |
| I | DNA:RNA | >50 | 67EC; 4 × SSC -or- 45EC; 4 × SSC, 50% formamide | 67EC; 1 × SSC |

TABLE I-continued

STRINGENCY CONDITIONS

| Stringency Condition | Poly-nucleotide Hybrid | Hybrid Length (bp)$^I$ | Hybridization Temperature and Buffer$^H$ | Wash Temperature and Buffer$^H$ |
|---|---|---|---|---|
| J | DNA:RNA | <50 | $T_J$; 4 × SSC | $T_J$; 4 × SSC |
| K | RNA:RNA | >50 | 70EC; 4 × SSC -or- 50EC; 4 × SSC, 50% formamide | 67EC; 1 × SSC |
| L | RNA:RNA | <50 | $T_L$; 2 × SSC | $T_L$; 2 × SSC |
| M | DNA:DNA | >50 | 50EC; 4 × SSC -or- 40EC; 6 × SSC, 50% formamide | 50EC; 2 × SSC |
| N | DNA:DNA | <50 | $T_N$; 6 × SSC | $T_N$; 6 × SSC |
| O | DNA:RNA | >50 | 55EC; 4 × SSC -or- 42EC; 6 × SSC, 50% formamide | 55EC; 2 × SSC |
| P | DNA:RNA | <50 | $T_P$; 6 × SSC | $T_P$; 6 × SSC |
| Q | RNA:RNA | >50 | 60EC; 4 × SSC -or- 45EC; 6 × SSC, 50% formamide | 60EC; 2 × SSC |
| R | RNA:RNA | <50 | $T_R$; 4 × SSC | $T_R$; 4 × SSC | bp$^1$: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarities.

buffer$^H$: SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete.

$T_B$ through $T_R$: The hybridization temperature for hybrids anticipated to be less than 50 base pairs in length should be 5-10EC less than the melting temperature ($T_m$) of the hybrid, where $T_m$ is determined according to the following equations. For hybrids less than 18 base pairs in length, $T_m(EC)=2(\#$ of A+T bases)+4(# of G+C bases). For hybrids between 18 and 49 base pairs in length, $T_m(EC)=81.5+16.6(\log_{10}[Na^+])+0.41(\% G+C)-(600/N)$, where N is the number of bases in the hybrid, and [Na$^+$] is the concentration of sodium ions in the hybridization buffer ([Na$^+$] for 1×SSC=0.165 M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference.

Embodiments of the invention also provide polynucleotides that are fully complementary to these polynucleotides and also provide antisense sequences. The antisense sequences, also referred to as antisense oligonucleotides, include both internally generated and externally administered sequences that block expression of polynucleotides encoding the polypeptides of the invention. The antisense sequences of the embodiments described herein include, for example, about 15-20 base pairs. The antisense sequences can be designed, for example, to inhibit transcription by preventing promoter binding to an upstream nontranslated sequence or by preventing translation of a transcript encoding a polypeptide of the invention by preventing the ribosome from binding.

The polynucleotides of the embodiments are prepared in many ways (e.g., by chemical synthesis, from DNA libraries, from the organism itself) and can take various forms (e.g., single-stranded, double-stranded, vectors, probes, primers). The term "polynucleotide" includes DNA and RNA, and also their analogs, such as those containing modified backbones. According to further embodiment, the polynucleotides comprise a DNA library, such as a cDNA library.

The methods of the various embodiments described herein include methods for detecting, identifying, and/or purifying the peptides and proteins described herein. Any suitable method is contemplated herein. According to one embodiment, the method for purifying a peptide or protein from a biological sample comprises: (1) contacting a biological sample thought to contain the peptide or protein described herein with one or more conjugating peptides to form conjugates; (2) isolating the resulting conjugates; and (3) separating the peptide or protein described herein from the one or more conjugates to obtain a purified peptide.

Preferably, one or more conjugating peptide has an amino acid sequence selected from the group consisting of:
   (i) A R L I (SEQ ID NO: 19);
   (ii) H A R L (SEQ ID NO: 2);
   (iii) F A R L (SEQ ID NO: 27);
   (iv) A R L (SEQ ID NO: 20); and
   (v) A R L C (SEQ ID NO: 30);

More preferably, the one or more conjugating peptides may comprise any of (i) to (v) above and at least one and up to 25 additional amino acids flanking either the 3' or 5' end of the peptide Even more preferably, the one or more conjugating peptides is selected from the group consisting of:
   (a) L H A R L C L A N F C G R N R V (SEQ ID NO: 4);
   (b) L A R L C L A N F C G N N N V (SEQ ID NO: 5);
   (c) C A R Y R T G H H A R L M (SEQ ID NO: 6);
   (d) H H A R L P L A N F C G (SEQ ID NO: 7);
   (e) R T G H H A R L C*L A N F C (SEQ ID NO: 8);
   (f) C E S A R Y R T G H H A R L C* (SEQ ID NO: 9);
   (g) D N T H H A R L I L (SEQ ID NO: 10);
   (h) S H H A R L I L (SEQ ID NO: 11); and homologs thereof Even more preferably, the one or more conjugating peptides has an amino acid sequence selected from the group consisting of:
   (a) H H A R L (SEQ ID NO: 1);
   (b) H A R L (SEQ ID NO: 2);
   (c) H A R L I (SEQ ID NO: 3);
   (d) H A R L I L (SEQ ID NO: 12);
   (e) H H A R L C L (SEQ ID NO: 13);
   (f) A R L I L (SEQ ID NO: 16);
   (g) H H A R L I F (SEQ ID NO: 17);
   (h) T H A R L I L (SEQ ID NO: 18);
   (i) A R L I (SEQ ID NO: 19);
   (j) A R L (SEQ ID NO: 20);
   (k) H A R L C L (SEQ ID NO: 21);
   (l) A R L C L (SEQ ID NO: 22);
   (m) A R C L (SEQ ID NO: 23);
   (n) M F A R L I L (SEQ ID NO: 24);
   (o) F A R L I L (SEQ ID NO: 25);
   (p) F A R L I (SEQ ID NO: 26);
   (q) F A R L (SEQ ID NO: 27);
   (r) H A R L I F (SEQ ID NO: 28);

(s) A R L I F (SEQ ID NO: 29); and homologs, derivatives or variants of such amino acid sequences.

The conjugates may be isolated from the biological sample using techniques and methods well known in the art. Likewise, the peptides and proteins described herein may be separated from the conjugated peptides in any manner known to persons skilled in the art. The biological source of peptide or protein used preferably is the urine of a patient diagnosed with AD. Before application to the column material, the biological sample preferably is processed in accordance with the teachings in U.S. patent application Ser. No. 09/697,590, filed Oct. 27, 2000, entitled: "Preferred Segments of Neural Thread Protein and Methods of Using the Same," the disclosure of which is incorporated by reference herein in its entirety.

Once the sample is prepared as described above, it is preferably conjugated to cyanogen bromide-activated agarose (Sigma, St. Louis, Mo.) according to the manufacturer's directions. Once prepared, the column material is stored in 25 mM TRIS buffered saline (TBS), pH 7, with 0.01% azide.

Subsequent to the conjugation, chromatography is preferably used as follows. 11 mL of the affinity column material is incubated for one hour with 25 mL of the urine sample (processed as described above to obtain a four times concentrated sample in TBS (pH 7)) and 25 mL of 0.025 M glycine buffer (pH 3.5). The unabsorbed material (pass through) is collected. The column is then washed with 5 volumes of 1× TBS (pH 7) and eluted in 11 mL of 0.1 M glycine (pH 2). Immediately following elution, the eluate is adjusted to pH 7 with NaOH, followed by concentration to 1 mL using an Amicon Centricon® YM-10 (Millipore, Beverly Mass.).

Preferably, analysis of peptide activity present in the affinity column eluate is then conducted. Affinity assay activity is assayed using strips or assays, which test for peptide in the urine ("Peptide Assay") (see, for example, Nymox Pharmaceutical Corp., Maywood N.J. See e.g., Fitzpatrick et al., *Alzheimer's Reports*, 3:155-159 (2000); de la Monte et al. *Front Biosci* 7: d989-96 (2002); Munzar et al. *Alzheimer's Reports* 5: 1-6 (2002); Munzar et al. *Neurol Clin Neurophysiol* 2002(1): 2-7 (2002); Munzar et al. *Alzheimer's Reports* 4: 61-65 (2001)).

The protein concentration in the eluate is preferably determined by Coomassie Blue staining (BioRad, Hercules, Calif.) (The starting protein concentration may be as determined by Bicinchoninic Acid Kit (Cat. # 23223, BioRad)). Absorbance is corrected for the buffer at 280 nm.

Gel electrophoresis preferably is used to analyze the Peptide from the Affinity Column Eluate as follows. 1 µg of the eluate (approximately 110-145 ng) is run on a 12.5% sodium dodecyl sulfate (SDS) mini-gel (Amersham Pharmacia Biotech, Sweden) and stained with silver and bands observed. The gel is sliced into the observed bands and placed in 100 µl of TBS, and allowed to dialyze against the TBS overnight. The band eluates are then concentrated using an Amicon Centricon® YM-10, and assayed for activity using the Peptide Assay. Reactivity is observed to determine whether the peptide is present.

The methods of the embodiments also include diagnostic tests, such as a test for determining the presence of AD or other neurodegenerative conditions. In accordance with an implementation, embodiments provide a diagnostic test for determining the presence of Alzheimer's Disease or other neurodegenerative disorder comprising (1) determining the amount of peptide having the amino acid sequence of SEQ ID NO:14 present in a biological sample; and (3) determining whether the amount of peptide having the amino acid sequence of SEQ ID NO:14 present in the sample is above a threshold amount indicative of the presence of Alzheimer's Disease or other neurodegenerative disorder. Preferred embodiments provide a diagnostic test for determining the presence of Alzheimer's Disease or other neurodegenerative disorder comprising: (1) contacting a biological sample with one or more conjugating peptides (2) determining the amount of peptide having the amino acid sequence of SEQ ID NO:14 present in the sample; and (3) determining whether the amount of peptide having the amino acid sequence of SEQ ID NO:14 present in the sample is above a threshold amount indicative of the presence of Alzheimer's Disease or other neurodegenerative disorder. Preferably, the conjugating peptides are those described above with regard to the method of purification.

The threshold amount indicative of the presence of Alzheimer's Disease or other neurodegenerative disorder preferably is at least about 22 µg/ml. Embodiments of the present invention also contemplate other thresholds to indicate stages of AD. These thresholds are readily determined by persons skilled in the art based upon the guidance provided herein.

Preferably the presence of the peptide of the preferred embodiments described herein is detected and quantified by using the conjugating peptides in the manner described in, for example, U.S. patent application Ser. No. 09/697,590, filed Oct. 27, 2000, entitled: "Preferred Segments of Neural Thread Protein and Methods of Using the Same."

It is preferred that the peptide and/or protein having the amino acid sequence identified in SEQ ID NO: 14 be used as a standard in the assay described herein for detecting AD, or other neurological disorders. The inventor has unexpectedly found that the assay described herein is effective in detecting the presence of AD in urine samples, wherein the peptide having the amino acid sequence identified in SEQ ID NO: 14 is used as a standard.

EXAMPLES

The following examples are provided to illustrate the present invention. It should be understood, however, that the embodiments described herein are not limited to the specific conditions or details described in these examples. Throughout the specification, any and all references to a publicly available document, including a U.S. patent, are specifically incorporated by reference.

Example 1

Identification of Peptide Detected by the Assay

Microtiter plates coated with one or more Harlil peptides described herein and rabbit immunoglobulins were used. Urine samples from subjects were processed as follows:

Using a sterile plastic container, first morning void urine samples were collected. A tablet of Stabilur (Globe Scientific) was added to the urine sample. The urine was immediately refrigerated at 4° C. for up to 24 h before processing. Samples were centrifuged at 3000 g for 15 min in a Sorval RC2-B centrifuge to remove cellular debris. The urine then was filtered using a Gelman syringe with a 0.22 µm cellulose acetate (Millipore) filter and the filtrate was brought to 0.05% sodium azide by adding 0.5% sodium azide 1:10 with filtered supernatant. This solution was then placed in the top of an Amicon Microcon YM-10 and centrifuged at 5000 rpm for 1 h and then reconstituted to the original volume with TBS. The Amicon YM-10 centrifugation and reconstitution step was then repeated twice for 30 min for each spin. The final retentate was reconstituted to 0.5 mL with TBS. This solution was then placed in the top of an Amicon Microcon YM-100 and centrifuged at 10 000 rpm for 5 min in a Fisher Scientific Marathon 13K/M centrifuge. The volume in the Microcon was diluted 1:14 in TBS.

Synthetic polypeptides shown in the Table below (SEQ ID NOS: 34-50, respectively, in order of appearance) were added to urine samples over a range of concentrations (0.01 to 5.0 mg/mL) and then treated as follows:

TABLE

| Number | Sequence |
|---|---|
| 1 | LQPSTPEIKHPPASASQVAGTKDMHHYT |
| 2 | FKLFSCPSLLSSWDYRRPPRLANFFVELVEMGFTMF |
| 3 | SSWDYGHLPPHPANFCIFIRGGVSPYLSGWSQTPDLR |
| 4 | ANFCGRNRVSLMCPSWSPELKQSTCLSLP |
| 5 | KCWDYRRAAVPGLFILFFLRHRCPTLTQDEVQWCDHSS |
| 6 | PASASQSAGITGV |
| 7 | FLVEMEFLHVGQAGLELPTSDDPSVSASQSARYRTGH |
| 8 | KCWDYRRAAVPGLFILFFLRHRCP |
| 9 | ILFFLRHRCPTLTQDEVQWCDHSS |
| 10 | AAVPGLFILFFLRHRCPTLTQDEV |
| 11 | CARYRTGHHARLM |
| 12 | DNTHHARLIL |
| 13 | PASAPVAGITGM |
| 14 | ISGPCDLPASASQSAGITGVSHHARLIFNFCLFEMESH |
| 15 | MEFSLLLPRLEC |
| 16 | NGAISAHRNLRL |
| 17 | WLIFIFIFNLRQSLNSVTQAGVQWRNLGSLQPLPPG |

A 50 μL volume of sample and 50 μL of alkaline phosphatase conjugated rabbit anti-mouse antibody were pipetted into each well and incubated for 60 minutes at room temperature, and washed three times with TBS/Tween 20 (0.05%) buffer; 150 μL of PNPP (Para Nitro Phenyl Phospate) (Moss, Pasadena, Md.) was then added and the color reaction was read on a Bio Rad 550 microplate reader at 405 nm (Bio Rad, Hercules, Calif.). Readings were derived from a standard curve constructed with Microplate Manager III using data from wells with recombinant AD7C-NTP.

Serial dilutions of peptide #14 provided consistent linear absorbance readings. It was, therefore, determined that the above method is able to determine the amount of this peptide or substances containing this peptide or fragments thereof in the sample.

Example 2

Using the same format as described above in example 1, using serial dilutions of sample #14 to generate a standard curve, samples of human serum albumin, acid-1-glycoprotein, human gamma globulin (100 μg/mL) and acetaminophen, alpraz, cephalex, diltiazem, furosemide, capoten, k-dur, fosamax, lanoxin, lipitor, losec, pepcid, vasotec, zoloft, adalat, atenolol, glyburide, hydrochlorthiazide, metoprolol, temazepam, amoxicillin, ativan, biaxin, demerol, indur, norvasc, tetracycline, synthroid, prozac, flurazepam, ibuprofen, coumadin, metformin and codeine phosphate (25 μg/mL) were mixed with normal processed urine samples. The UV absorption of these urine samples were read as in example 1. The above substances had no effect on the absorbance readings, when compared to normal urine.

Example 3

Urine samples from 20 normal individuals were tested in the same format as described above in example 1, using serial dilutions of sample #14 to generate a standard curve. The absorbance readings of the 20 normal individuals was consistently in the range of 0.961 to 1.310.

Example 4

Urine samples from 20 cases of AD and 20 cases of non-AD individuals were tested as described in example 1 above, using serial dilutions of sample #14 to generate a standard curve. The absorbance readings of the 20 normal individuals were in the range of 0.961 to 1.310. The readings for the AD individuals was in the range of 0.169 to 0.754.

The above examples indicate that individuals with AD have in their urine certain protein substances in quantities not found in normal subjects. These protein substances have also been determined to contain part or all of the amino acid sequence contained in SEQ ID NO: 14. For example, the protein in the urine may contain this sequence in part or in whole.

This assay and related methods have diagnostic and therapeutic utility. It was further unexpectedly found that the polypeptide having the amino acid sequence of SEQ ID NO: 14 could be serially diluted and used to estimate the quantity of similar or identical substance(s) in the urine of the individuals being tested.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. An isolated peptide consisting of the amino acid sequence of SEQ ID NO:14.

2. The peptide of claim 1, wherein the peptide is substantially pure.

3. The peptide of claim 1, wherein the peptide is a recombinant peptide.

4. An isolated peptide consisting of a peptide consisting of the amino acid sequence of SEQ ID NO: 14 conjuated to a conjugating peptide consisting of the amino acid sequence of SEQ ID NO: 12.

5. An isolated peptide encoded by the nucleic acid sequence consisting of SEQ ID NO:15.

6. A composition comprising an isolated peptide consisting of the amino acid sequence of SEQ ID NO:14.

7. The composition of claim 6, additionally comprising a carrier.

* * * * *

SEQUENCE LISTING

```
<160> NUMBER OF SEQ ID NOS: 50

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His His Ala Arg Leu
 1               5
```

```
<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Ala Arg Leu
  1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Ala Arg Leu Ile
  1               5

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu His Ala Arg Leu Cys Leu Ala Asn Phe Cys Gly Arg Asn Arg Val
  1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Ala Arg Leu Cys Leu Ala Asn Phe Cys Gly Asn Asn Asn Val
  1               5                  10                  15

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Ala Arg Tyr Arg Thr Gly His His Ala Arg Leu Met
  1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

His His Ala Arg Leu Pro Leu Ala Asn Phe Cys Gly
 1               5                  10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Thr Gly His His Ala Arg Leu Cys Leu Ala Asn Phe Cys
 1               5                  10

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Glu Ser Ala Arg Tyr Arg Thr Gly His His Ala Arg Leu Cys
 1               5                  10                  15

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Asn Thr His His Ala Arg Leu Ile Leu
 1               5                  10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser His His Ala Arg Leu Ile Leu
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Ala Arg Leu Ile Leu
 1               5

<210> SEQ ID NO 13
<211> LENGTH: 7
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 13

His His Ala Arg Leu Cys Leu
 1               5

<210> SEQ ID NO 14
<211> LENGTH: 38
<212> TYPE: PRT
<213> ORGANISM: Homo sapiens

<400> SEQUENCE: 14

Ile Ser Gly Pro Cys Asp Leu Pro Ala Ser Ala Ser Gln Ser Ala Gly
 1               5                  10                  15

Ile Thr Gly Val Ser His His Ala Arg Leu Ile Phe Asn Phe Cys Leu
                20                  25                  30

Phe Glu Met Glu Ser His
            35

<210> SEQ ID NO 15
<211> LENGTH: 114
<212> TYPE: DNA
<213> ORGANISM: Homo sapiens
<220> FEATURE:
<221> NAME/KEY: CDS
<222> LOCATION: (1)..(114)

<400> SEQUENCE: 15 atc tct gga cct tgt gat ctg cct gcc tcg gcc tcc caa agt gct ggg      48
Ile Ser Gly Pro Cys Asp Leu Pro Ala Ser Ala Ser Gln Ser Ala Gly
 1               5                  10                  15 att aca ggc gtg agc cac cac gcc cgg ctt att ttt aat ttt tgt ttg      96
Ile Thr Gly Val Ser His His Ala Arg Leu Ile Phe Asn Phe Cys Leu
                20                  25                  30 ttt gaa atg gaa tct cac                                             114
Phe Glu Met Glu Ser His
            35

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Arg Leu Ile Leu
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His His Ala Arg Leu Ile Phe
 1               5
```

```
<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr His Ala Arg Leu Ile Leu
 1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Arg Leu Ile
 1

<210> SEQ ID NO 20
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Arg Leu
 1

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

His Ala Arg Leu Cys Leu
 1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Arg Leu Cys Leu
 1               5

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

```
Ala Arg Cys Leu
  1

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Phe Ala Arg Leu Ile Leu
  1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Phe Ala Arg Leu Ile Leu
  1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Ala Arg Leu Ile
  1               5

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Ala Arg Leu
  1

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Ala Arg Leu Ile Phe
  1               5

<210> SEQ ID NO 29
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 29

Ala Arg Leu Ile Phe
 1               5

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Arg Leu Cys
 1

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Ser Trp Asp Tyr
 1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His Ala Arg Leu Met Leu
 1               5

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ile Thr Gly Met Cys Thr His Ala Arg Leu Ile Leu Tyr Phe Phe
 1               5                  10                  15

Leu Val

<210> SEQ ID NO 34
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Gln Pro Ser Thr Pro Glu Ile Lys His Pro Pro Ala Ser Ala Ser
```

```
                    1               5                  10                  15
Gln Val Ala Gly Thr Lys Asp Met His His Tyr Thr
                    20                  25
```

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Phe Lys Leu Phe Ser Cys Pro Ser Leu Leu Ser Ser Trp Asp Tyr Arg
  1               5                  10                  15
Arg Pro Pro Arg Leu Ala Asn Phe Phe Val Glu Leu Val Glu Met Gly
                    20                  25                  30
Phe Thr Met Phe
                35
```

<210> SEQ ID NO 36
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Ser Ser Trp Asp Tyr Gly His Leu Pro Pro His Pro Ala Asn Phe Cys
  1               5                  10                  15
Ile Phe Ile Arg Gly Gly Val Ser Pro Tyr Leu Ser Gly Trp Ser Gln
                    20                  25                  30
Thr Pro Asp Leu Arg
                35
```

<210> SEQ ID NO 37
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Ala Asn Phe Cys Gly Arg Asn Arg Val Ser Leu Met Cys Pro Ser Trp
  1               5                  10                  15
Ser Pro Glu Leu Lys Gln Ser Thr Cys Leu Ser Leu Pro
                    20                  25
```

<210> SEQ ID NO 38
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Lys Cys Trp Asp Tyr Arg Arg Ala Ala Val Pro Gly Leu Phe Ile Leu
  1               5                  10                  15
Phe Phe Leu Arg His Arg Cys Pro Thr Leu Thr Gln Asp Glu Val Gln
                    20                  25                  30
```

```
Trp Cys Asp His Ser Ser
            35

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Pro Ala Ser Ala Ser Gln Ser Ala Gly Ile Thr Gly Val
 1               5                  10

<210> SEQ ID NO 40
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Leu Val Glu Met Glu Phe Leu His Val Gly Gln Ala Gly Leu Glu
 1               5                  10                  15

Leu Pro Thr Ser Asp Asp Pro Ser Val Ser Ala Ser Gln Ser Ala Arg
                20                  25                  30

Tyr Arg Thr Gly His
            35

<210> SEQ ID NO 41
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Cys Trp Asp Tyr Arg Arg Ala Ala Val Pro Gly Leu Phe Ile Leu
 1               5                  10                  15

Phe Phe Leu Arg His Arg Cys Pro
                20

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Leu Phe Phe Leu Arg His Arg Cys Pro Thr Leu Thr Gln Asp Glu
 1               5                  10                  15

Val Gln Trp Cys Asp His Ser Ser
                20

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 43

Ala Ala Val Pro Gly Leu Phe Ile Leu Phe Leu Arg His Arg Cys
  1               5                  10                  15

Pro Thr Leu Thr Gln Asp Glu Val
                20

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Ala Arg Tyr Arg Thr Gly His His Ala Arg Leu Met
  1               5                  10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Asn Thr His His Ala Arg Leu Ile Leu
  1               5                  10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Pro Ala Ser Ala Pro Val Ala Gly Ile Thr Gly Met
  1               5                  10

<210> SEQ ID NO 47
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Ser Gly Pro Cys Asp Leu Pro Ala Ser Ala Ser Gln Ser Ala Gly
  1               5                  10                  15

Ile Thr Gly Val Ser His His Ala Arg Leu Ile Phe Asn Phe Cys Leu
                20                  25                  30

Phe Glu Met Glu Ser His
            35

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 48

Met Glu Phe Ser Leu Leu Leu Pro Arg Leu Glu Cys
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asn Gly Ala Ile Ser Ala His Arg Asn Leu Arg Leu
1               5                   10

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Leu Ile Phe Ile Phe Ile Phe Asn Leu Arg Gln Ser Leu Asn Ser
1               5                   10                  15

Val Thr Gln Ala Gly Val Gln Trp Arg Asn Leu Gly Ser Leu Gln Pro
            20                  25                  30

Leu Pro Pro Gly
            35
```